(12) United States Patent
Oku et al.

(10) Patent No.: US 6,803,490 B2
(45) Date of Patent: Oct. 12, 2004

(54) PROCESS FOR PRODUCING α-PHENYLETHYL ALCOHOL

(75) Inventors: Noriaki Oku, Ichihara; Hirofumi Koike, Sodegaura, both of (JP)

(73) Assignee: Sumitomo Chemical Company, Limited, Osaka (JP)

(*) Notice: Subject to any disclaimer, the term of this patent is extended or adjusted under 35 U.S.C. 154(b) by 587 days.

(21) Appl. No.: 09/757,461

(22) Filed: Jan. 11, 2001

(65) Prior Publication Data

US 2004/0162449 A1 Aug. 19, 2004

(30) Foreign Application Priority Data

Jan. 12, 2000 (JP) ........................................ 2000-003561

(51) Int. Cl.$^7$ .............................................. C07C 27/00
(52) U.S. Cl. ..................................................... 568/814
(58) Field of Search ........................................ 568/814

(56) References Cited

U.S. PATENT DOCUMENTS 4,996,374 A    2/1991  Lin et al.
6,046,369 A    4/2000  Oku et al.

FOREIGN PATENT DOCUMENTS

| DE | 3933661 C2 | 4/1991 |
| EP | 0714877 A2 | 6/1996 |
| JP | 53-25503 | 3/1978 |
| JP | 1272540 A | 10/1989 |
| JP | 278639 A | 3/1990 |
| NL | 7709128 | 1/1978 |

*Primary Examiner*—Michael L. Shippen
(74) *Attorney, Agent, or Firm*—Birch, Stewart, Kolasch & Birch, LLP

(57) ABSTRACT

A process for producing α-phenylethyl alcohol, which comprises supplying a raw material containing acetophenone into a reactor and hydrogenating acetophenone in the presence of a hydrogenation catalyst, wherein the concentrations of organic acids and sulfur-containing acids in the raw material containing acetophenone are 1 μmol/g or less and 0.5 μmol/g or less, respectively.

4 Claims, No Drawings

PROCESS FOR PRODUCING α-PHENYLETHYL ALCOHOL

BACKGROUND OF THE INVENTION

1. Field of the Invention

The present invention relates to a process for producing α-phenylethyl alcohol. More particularly, the present invention relates to, in a process for producing α-phenylethyl alcohol by hydrogenating acetophenone in the presence of a catalyst, a process which can keep the lowering of catalyst activity with use at an extremely low level.

2. Description of Related Arts

It is known that α-phenylethyl alcohol can be produced by hydrogenating acetophenone in the presence of a catalyst. α-phenylethyl alcohol is useful, for example, as a raw material for production of styrene or a raw material for production of various perfumes.

For example, JP-A-59027216 discloses a process for hydrogenating acetophenone with a copper-chromite catalyst which contains barium, zinc and magnesium, as a copper-based catalyst.

By the way, when a hydrogenation is conducted by flowing a raw material containing acetophenone through a hydrogenation catalyst, there have been problems that the catalyst activity is lowered remarkably, the quality of the catalyst cannot be sufficiently exhibited over long period, and it is particularly disadvantageous from the industrial view point.

SUMMARY OF THE INVENTION

As a result of extensive study, the present inventors have found that a trace amount of organic acids and sulfur-containing acids was contained in a raw material containing acetophenone (herein-after, sometimes referred to simply as "raw material") and these impurities caused to deactivation of the catalyst. As a result of further study, the present inventors have found that the lowering of catalyst activity with use can be kept at an extremely low level by reducing concentrations of the organic acids and the sulfur-containing acids in the raw material to less than specific amounts and completed the present invention.

Namely, the present invention relates to a process for producing α-phenylethyl alcohol which comprises supplying a raw material containing acetophenone into a reactor, and hydrogenating acetophenone in the presence of a hydrogenating catalyst, wherein concentrations of organic acids and sulfur-containing acids in the raw material containing acetophenone are 1 $\mu$mol/g or less and 0.5 $\mu$mol/g or less, respectively.

DETAILED DESCRIPTION OF THE INVENTION

The catalyst used in the present invention is a catalyst for hydrogenating acetophenone to provide α-phenylethyl alcohol, and includes, for example, a copper-based catalyst and a noble metal catalyst. As the copper-based catalyst, catalysts disclosed in JP-B59-027216, EP-B-714877 and DE-B-3933661 can be mentioned. Herein, the copper-based catalyst means a catalyst containing CuO as a main component. The content of CuO in the catalyst is usually 10 to 90% by weight and preferably 20 to 80% by weight. The too low and too high amount of the content happen to cause the lowering of hydrogenation activity. The components other than CuO in the catalyst include various metal oxides such as $Cr_2O_3$, ZnO, $Fe_2O_3$, $Al_2O_3$, $La_2O_3$, $Sm_2O_3$, $CeO_2$, $TiO_2$, $SiO_2$, $MnO_2$, $Co_2O_3$, NiO, BaO, CaO, MgO and the like, and a compound oxide-based catalyst in which CuO—$Cr_2O_3$ and CuO—ZnO are main components is suitably used. Further, an alkaline metal compound may be contained as a component other than the above-mentioned components. As the noble metal catalyst, catalysts containing Pd, Rh, Pt or Ru are mentioned. As the example, catalysts disclosed in U.S. Pat. No. 4,996,374, JP-B-1-272540 and JP-B-2-78639 can be mentioned, but catalysts are not limited thereto.

The catalyst used in the present invention may be a catalyst using a carrier or a catalyst not using a carrier. The carrier includes metal oxides and compound oxides thereof such as silica, alumina, titania, zirconia, magnesia, silica-alumina and the like; bentonite, montmorillonite, diatomaceous earth, acid clay, activated carbon and the like, but silica and diatomaceous earth are preferable. Further, when the catalyst is molded, binders such as graphite, silica sol, alumina and the like may be added.

The catalyst can be produced by a co-precipitation method, a precipitation method, a mixing method or the like. For example, a catalyst powder is prepared by heating a paste obtained by the co-precipitation method, the forementioned binder or the like is added to the powder, and a molded pellet is prepared by a tabletting molding or an extrusion molding.

Further, commercially available products corresponding thereto may be used.

As the reaction form in hydrogenation, any one of a slurry process, a fixed-bed process or a fluidized bed process can be applied.

The hydrogenation of acetophenone is carried out using the above-mentioned catalyst. The reaction temperature is usually from 40 to 200° C., and preferably from 60 to 150° C. The reaction pressure is usually from 0.1 to 20 Mpa and preferably from 1 to 10 Mpa. When the temperature or pressure is too low, the reaction does not adequately proceed, and on the other hand, when the temperature or pressure is too high, by-production of ethylbenzene may increase. In case of the fixed-bed process, the amount of a catalyst used is usually from 0.01 to 50 hr$^{-1}$ in terms of the space velocity of the raw material to a catalyst layer and preferably from 0.1 to 20 hr$^{-1}$. In case of the slurry process, the amount of the catalyst is usually from 0.01 to 20% by weight based on the weight of acetophenone contained in the raw material and preferably from 0.1 to 10% by weight. The amount of hydrogen supplied is usually from 1 to 3-fold by mole for the amount of acetophenone in the raw material liquid supplied.

The concentration of the organic acids (excluding sulfur-containing organic acids) in the raw material liquid for reaction used in the present invention is 1 $\mu$mol/g or less and preferably 0.5 $\mu$mol/g or less, and the concentration of the sulfur-containing acids is 0.5 $\mu$mol/g or less and preferably 0.1 $\mu$mol/g or less. Thereby, the lowering of catalyst activity with use can be kept at an extremely low.

Herein, the organic acids as impurities include carboxylic acids (e.g. formic acid, acetic acid, propionic acid, lactic acid) (proviso excluding organic sulfur-containing acids). And, the sulfur-containing acids as impurities include sulfur-containing inorganic acids (e.g. sulfuric acid) and sulfur-containing organic acids(e.g. p-toluene sulfonic acid).

The concentrations of the organic acids and the sulfur-containing acids in the raw material can be measured according to an ion chromatography, a liquid chromatography, a gas chromatography, a neutralization titration or the like.

As a method of reducing the concentrations of the acids in the raw material to within the scope of the present invention, for example, a method of washing the raw material with water or a basic aqueous solution can be mentioned. The basic aqueous solution includes aqueous solution containing a base such as a metal hydroxide, a metal carbonate, a metal bicarbonate, ammonia, an amine or the like. The metal includes sodium, potassium, lithium, calcium and the like.

Further, other methods include a contact treatment of the raw material with an absorber such as an ion-exchange resin, a method such as distillation, absorption or the like, and the like can be mentioned.

As the raw material, only acetophenone may be used, but a mixed solution containing other impurities or the like in addition to acetophenone may be used, so far as the purpose of the present invention is not damaged. Further, a solution in which an appropriate solvent is added may be used. The solvent includes alcohols such as methanol, ethanol, propanol, ethylene glycol monomethyl ether, α-phenylethyl alcohol and the like; ethers such as diethyl ether, tetrahydrofuran, dioxane, ethylene glycol dimethyl ether and the like; hydrocarbons such as hexane, heptane, toluene, ethyl benzene and the like; and mixed solvents thereof. When the solvent is used, the amount of the solvent used is usually from 0.5 to 10-fold by weight for acetophenone. Such dilution of the raw material is effective for keeping a high selectivity of the reaction.

Further, a portion of the reaction liquid after hydrogenation may be recycled to the raw material liquid. The recycling of the portion of the reaction liquid enables the effective removal of the reaction heat, and is effective for keeping the selectivity of reaction high.

EXAMPLE

The present invention is illustrated in detail using Examples below.

Example 1

In a reaction tube having an inner diameter of 1 cm and a packing height of 1 m of a fixed bed adiabatic reactor, 70 cc of a copper silica pellet catalyst (containing 65% by weight of CuO) was filled, 400 g/hr of a flesh raw material liquid composed of 20% by weight of acetophenone (hereinafter, described as "ACP"), 10% by weight of α-phenylethyl alcohol (hereinafter, described as "MBA"), 55% by weight of ethylbenzene (hereinafter, described as "EB"), and 15% by weight of other compounds, and 35.6 NL/hr converted to normal state (the molar ratio of hydrogen to acetophenone contained in the raw material is 1.98-fold by mol) of a mixed gas composed of 83% by volume of hydrogen and 17% by volume of methane were fed, and hydrogenation was carried out at 2.5 MPa (24 kg/cm$^2$G). At a steady state in which the inlet temperature of the reactor is controlled at 91° C., reaction results determined from compositions at the inlet and exit of the reactor were 90.8% as an ACP conversion after 20 hours from start of the reaction, and 85% after 42 hours. The concentration of organic acids in the raw material was 0.02 μmol/g, and the concentration of sulfur-containing acids was 0.001 μmol/g.

Example 2

In a reaction tube having an inner diameter of 1 cm and a packing height of 0.2 m of a fixed bed reactor, 14 cc of a copper silica pellet catalyst (containing 65% by weight of CuO) was filled, 210 g/hr of a flesh raw material solution composed of 45% by weight of ACP, 40% by weight of MBA, and 15% by weight of other compounds, and 35.6 NL/hr converted to normal state (the molar ratio of hydrogen to acetophenone contained in the raw material is 1.75-fold by mol) of a mixed gas composed of 87% by volume of hydrogen and 13% by volume of methane were fed, and hydrogenation was carried out at 2.5 MPa (24 kg/cm$^2$G). At a steady state in which the temperature of an oil bath is established at 95° C., a reaction result determined from composition at the inlet and exit of the reactor after 5 hours was 6.5% as an ACP conversion. Further, the concentration of organic acids in the raw material was 0.01 μmol/g, and the concentration of sulfur-containing acids was 0.001 μmol/g.

Comparative Example 1

When the raw material which is fed to the reactor in Example 1 was replaced with a raw material having an organic acid concentration of 0.12 μmol/g, the ACP conversion is abruptly lowered to 69.9% after 2 hours, and is lowered to 66% for additional 2 hours thereafter, and the activity was drastically lowered.

Comparative Example 2

When the raw material which is fed to the reactor in Example 2 was replaced with a raw material having an organic acid concentration of 0.52 μmol/g, the ACP conversion is abruptly lowered to a conversion of 0.2%, and hydrogenation activity was hardly exhibited after additional 5 hours thereafter.

As described above, according to the present invention, in a process for producing α-phenylethyl alcohol by hydrogenating acetophenone in the presence of a hydrogenation catalyst, a process which can keep the lowering of catalyst activity with use at an extremely low level can be provided.

What is claimed is:

1. A process for producing α-phenylethyl alcohol, which comprises supplying a raw material containing acetophenone into a reactor and hydrogenating acetophenone in the presence of a hydrogenation catalyst, wherein the concentrations of organic acids and sulfur-containing acids in the raw material containing acetophenone are 1 μmol/g or less and 0.5 μmol/g or less, respectively.

2. The process according to claim 1, wherein the concentration of organic acids is 0.5 μmol/g or less and the concentration of sulfur-containing acids is 0.1 μmol/g or less.

3. The process according to claim 1, wherein the hydrogenation catalyst is a copper-based catalyst or noble metal catalyst.

4. The process according to claim 2, wherein the hydrogenation catalyst is a copper-based catalyst or noble metal catalyst.

* * * * *